(12) United States Patent
Grace

(10) Patent No.: US 6,535,836 B1
(45) Date of Patent: Mar. 18, 2003

(54) METHOD FOR THE ANALYSIS OF ABNORMAL PARTICLE POPULATIONS

(75) Inventor: Eric Malcolm Grace, Cooper City, FL (US)

(73) Assignee: Coulter International Corp., Miami, FL (US)

( * ) Notice: Subject to any disclaimer, the term of this patent is extended or adjusted under 35 U.S.C. 154(b) by 139 days.

(21) Appl. No.: 09/677,076

(22) Filed: Sep. 29, 2000

(51) Int. Cl.[7] .............................................. G01N 27/00
(52) U.S. Cl. ........................ 702/179; 702/19; 702/21; 702/23; 702/50; 702/180; 702/183
(58) Field of Search ...................... 702/19, 21, 22, 702/23, 26, 27, 28, 29–32, 45, 49, 50, 66, 67, 78, 179, 180, 183, 128, 189, FOR 103–FOR 105, FOR 109, FOR 110, FOR 115–FOR 119, FOR 127–FOR 128, FOR 131, FOR 134, FOR 139–FOR 140, FOR 170–FOR 171; 700/266, 273; 600/368; 422/81, 82.08, 82.09; 436/52; 356/28.5, 336, 342

(56) References Cited

U.S. PATENT DOCUMENTS

| | | | | |
|---|---|---|---|---|
| 3,949,198 A | * | 4/1976 | Coulter et al. | 235/92 PC |
| 3,963,983 A | * | 6/1976 | Hogg | 324/71 CP |
| 4,263,508 A | * | 4/1981 | Leary et al. | 250/358 R |
| 4,338,564 A | * | 7/1982 | Mundschenk | 324/71 CP |
| 4,710,021 A | * | 12/1987 | von Behrens | 356/72 |
| 4,817,446 A | | 4/1989 | Kanamori | |
| 4,933,884 A | * | 6/1990 | Lorenz | 364/555 |
| 5,187,673 A | * | 2/1993 | Carver, Jr. et al. | 364/555 |
| 5,296,910 A | * | 3/1994 | Cole | 356/28.5 |
| 5,349,538 A | * | 9/1994 | Carver, Jr. et al. | 364/565 |
| 5,359,906 A | * | 11/1994 | Kanai | 73/865.5 |
| 5,452,237 A | * | 9/1995 | Jones, Jr. | 364/555 |
| 5,532,943 A | * | 7/1996 | Asano et al. | 364/555 |
| 5,555,198 A | * | 9/1996 | Asano | 364/555 |
| 5,604,431 A | * | 2/1997 | Serna | 324/71.4 |
| 5,690,105 A | * | 11/1997 | Shibata et al. | 73/865.5 |
| 5,728,351 A | * | 3/1998 | Carver, Jr. | 422/73 |
| 5,735,274 A | * | 4/1998 | Shibata et al. | 128/637 |
| 5,795,506 A | * | 8/1998 | Hodosawa et al. | 264/4.1 |
| 5,840,254 A | * | 11/1998 | Carver, Jr. et al. | 422/68.1 |
| 5,845,237 A | * | 12/1998 | Puel et al. | 702/179 |
| 5,907,240 A | * | 5/1999 | Carver, Jr. et al. | 324/71.1 |
| 6,030,838 A | | 2/2000 | Telmissani | |
| 6,122,599 A | * | 9/2000 | Mehta | 702/100 |
| 6,141,624 A | * | 10/2000 | Kasdan et al. | 702/23 |
| 6,181,319 B1 | * | 1/2001 | Fujita et al. | 345/134 |
| 6,246,786 B1 | * | 6/2001 | Nishikiori et al. | 382/134 |

\* cited by examiner

*Primary Examiner*—Marc S. Hoff
*Assistant Examiner*—Carol S. W. Tsai
(74) *Attorney, Agent, or Firm*—Mary E. Bak; Mitchell E. Alter

(57) ABSTRACT

A method for analyzing an abnormal particle population in an experimental sample containing particles involves a particle property distribution index based on an average particle property (e.g., size) distribution curve for multiple normal samples in a particle analysis instrument. The process involves producing an experimental particle property distribution curve by analyzing an experimental sample containing particles in the instrument. The distribution curve of the experimental sample is analyzed to identify particle populations at the lower or upper region of the experimental distribution curve that differ from particle populations in the regions of an average particle property distribution curve. Thereafter, the number of particles within the lower or upper region of the experimental distribution curve that differs from the average curve is determined and employed for diagnosis of a relevant characteristic of the particle population. A computer program which makes calculations for such methods can be employed or can be integrated into a particle analysis instrument. The method, program, and instruments of this invention provide a novel red blood cell parameter.

29 Claims, 5 Drawing Sheets

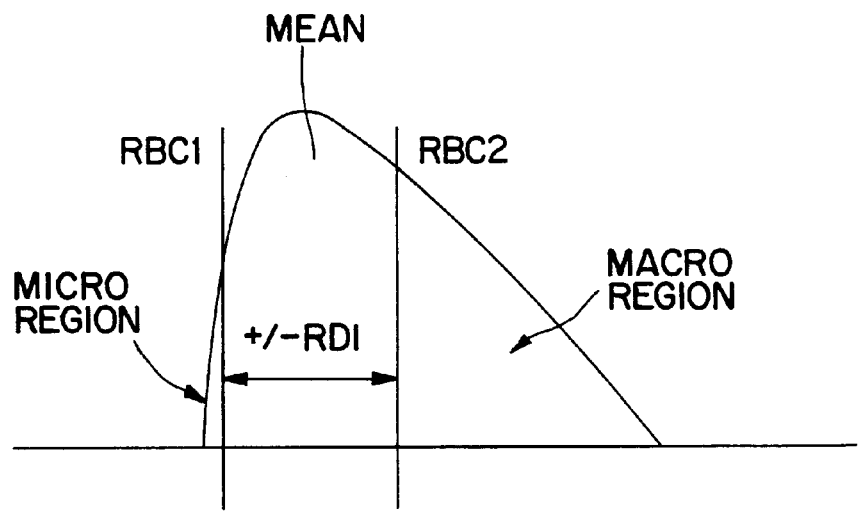
F I G. 4
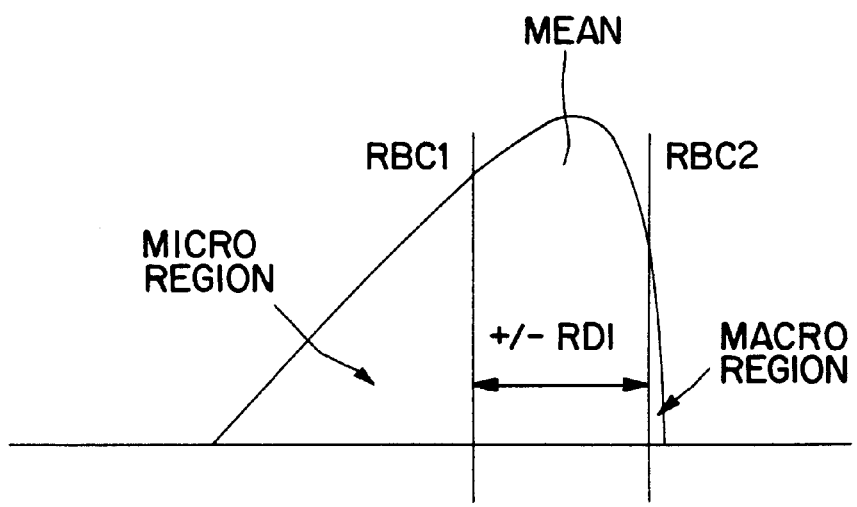
F I G. 5

METHOD FOR THE ANALYSIS OF ABNORMAL PARTICLE POPULATIONS

FIELD OF THE INVENTION

The present invention relates to the field of measuring and analyzing particle distributions. More specifically, the invention relates to a method for analyzing aberrant biological cell populations, particularly hematological populations.

BACKGROUND OF THE INVENTION

Certain particle size populations that have a typical size distribution are commonly measured and reported by means of a relatively constant mathematical size distribution curve. Among such populations are included red blood cells, bacterial cells, latex particles and other fine particles. Certain characteristics of particle size distributions have been made by comparing sample size distribution data with average, normal size distribution data for the same particles. See, for example, the methods described in U.S. Pat. No. 4,817,446.

Current automated particle size analysis instruments use one or more parameters of light scatter, fluorescence, volume measured by direct current (D.C.), (Coulter) volume, and high frequency (radio frequency), to provide data used to analyze characteristics or properties of particles. Of particular interest are those characteristics or properties of particles that can be used to create a particle distribution curve. For example, some of these instruments are based on the Coulter Principle of detection and measurement of changes in electrical impedance produced when particles (e.g., cells) suspended in a conductive diluent pass through an aperture. Submerged electrodes, through which constant current passes, are located on either side of the aperture. As a dilute suspension of cells is drawn through the aperture, the passage of individual cells momentarily increases the impedance of the electrical path between the two submerged electrodes. See, e.g., FIG. 2. While the number of electrical pulses (i.e., a pulse indicates the time for a specified voltage to pass through the particle and return to a baseline value) indicates cell count, amplitude of the pulses corresponds to cell volume.

A histogram is a graphical representation of the frequency distribution of the cells. By electronically sorting the cells by pulse size (cell volume) and placing each pulse into "buckets" or channels according to the size of the pulse, a histogram can be created. The sorted pulses are displayed as a histogram with volume on the X-axis and pulse frequency (number) on the Y-axis. This process is called channelyzation. The number of channels into which the X-axis is divided, and the size range covered by the channelyzer is fixed in the design of the particular hematology analyzer. These parameters are dependent on the cell population being analyzed and the sensitivity (resolution) required.

Histograms graphically show a cell population's shape and its spread (i.e., variation around the mean). Thus, histograms provide an assessment of red blood cell (RBC) morphology by the measurement of cell size, Mean Cell Volume (MCV) and Red Cell Distribution Width (RDW). MCV is a measure of the average cell volume in the population (i.e., the population mean). RDW is a measure of the amount of dispersion (or anisocytosis) or heterogeneity in the RBC population. A resulting RBC histogram is typically Gaussian in shape and the distribution of the red cells about the mean is reasonably constant within a population of normal samples. See, for example, FIG. 1.

There is a need in the art for additional methods for determining and identifying particle distributions that fall outside the average histogram mean, or mean of other types of particles. Such particle distributions aid in the diagnosis of disease by differentiating abnormal blood samples from normal blood samples, particularly where the distribution of the particles falling outside of the mean of such "normal" particles is evidence of such abnormality.

SUMMARY OF THE INVENTION

In one aspect, the invention provides a method for analyzing an abnormal particle population in an experimental sample containing the particles. The method comprises, as one step, analyzing a particle property distribution curve of the experimental sample in a particle analysis instrument. The instrument provides electrical pulse data of a property of the particle recorded as a range of channel volume numbers and pulse frequency data. A plot of pulse frequency vs. channel number produces a particle property distribution curve. The analysis step is performed to identify particle populations at the lower or upper region of the experimental distribution curve that differ from particle populations in the same regions of an average particle property distribution curve. The average curve is based on multiple normal samples containing the same type of particle. Further, the method includes the step of determining the number or percentage of particles within the lower or upper region of the experimental distribution curve to identify a characteristic of the sample. An increase or decrease in the percentage or number of particles of the experimental sample in these regions of the curve in comparison to the percentage or number in the same regions of the average curve indicates an abnormal particle population in that region. Such an abnormal population of particles is a characteristic of the experimental sample that can be used for diagnosis of disease or evaluation of a product, depending upon the nature of the particles evaluated. In a particularly preferred embodiment, the particle property is particle size.

In one embodiment, the method also provides the steps of determining a particle property distribution index based on the average particle property distribution curve in the particle analysis instrument. The method further involves comparing the average particle property distribution curve and the experimental particle property distribution curve by analyzing curve data using the index. In a particularly preferred embodiment, the particle property is particle size.

In another aspect, the invention provides a method for analyzing an abnormal red blood cell population in an experimental sample comprising the steps of analyzing a red blood cell size distribution curve of the experimental sample in a hematology instrument. This instrument provides electrical pulse size data recorded as a range of channel volume numbers and pulse frequency data. A plot of pulse frequency vs. channel number produces the red blood cell size distribution curve. Red blood cell populations at the lower or upper region of the experimental distribution curve that differ from red blood cell populations in the same regions of an average red blood cell size distribution curve based on multiple normal samples are identified. The number or percentage of red blood cells within the lower or upper region of the experimental distribution curve is determined to identify a characteristic of the sample.

In another aspect, the invention provides an improvement in methods for analyzing particle population in an experimental sample. The method includes the steps of evaluating the sample in a particle size analysis instrument that measures the size and frequency of electrical impedance pulses produced when each particle in a conductive diluent passes through a constant current. This instrument provides pulse size data recorded as a range of channel volume numbers and pulse frequency data. A plot of pulse frequency vs. channel number produces the particle size distribution curve. In such methods, an experimental sample size distribution curve is compared with an average size distribution curve for normal samples of the same particles. The improvement comprises the steps of: (a) identifying differences in the particle populations at the lower or upper region of the experimental sample distribution curve from similarly located particle populations of the average particle size distribution curve; and (b) quantifying the number or percentage of particles within the lower or upper region of the experimental distribution curve that differs from the average curve by an analysis using a particle size distribution index.

In still another aspect, the invention provides a computer program that implements the methods described above. The program implements or performs the following analytical steps in concert with data generated by a particle analysis instrument. An experimental particle property (e.g., size) distribution curve is produced by analyzing an experimental sample containing particles in a particle analysis instrument. The distribution curve of the experimental sample is analyzed to identify particle populations at the lower or upper region of the experimental distribution curve that differ from particle populations in the regions of an average particle property distribution curve based upon normal samples. The program also quantifies the number or percentage of particles within the lower or upper region of the experimental distribution curve. Sorted experimental data is analyzed using a particle property distribution index based on an average particle property distribution curve for multiple normal samples. An increase in the number or percentage of the particles in the lower or upper region identifies a characteristic of the sample. Finally, the program permits the identification of a deviation from the average normal samples in the region by generating an electrical signal.

In yet a further aspect, the invention provides a particle analysis instrument that comprises a computer program as described above. In one aspect, the computer program is integrated into the analysis instrument. In another aspect, the computer program is provided in a separate computer that is a standalone instrument into which is fed data provided by the analysis instrument. In still another aspect, the computer program is associated with the analysis instrument as part of a "plug-in" device that can be connected to the instrument.

In still another aspect, the invention provides a parameter for analyzing conditions associated with aberrant red blood cell populations in a histogram. The "Micro" parameter is defined as the percentage or number of cells in the region of the histogram spanning the beginning of the experimental sample distribution curve to a threshold related to a particle size distribution index.

In a further aspect, the invention provides another parameter for analyzing conditions associated with aberrant red blood cell populations in a histogram. This "Macro" parameter is defined as the percentage of cells in the region of the histogram spanning a threshold related to a particle size distribution index and the end of the experimental sample distribution curve.

Other aspects and advantages of the present invention are described further in the following detailed description of the preferred embodiments thereof.

BRIEF DESCRIPTION OF THE DRAWINGS

FIG. 4 is an abnormal RBC size distribution curve with the same MCV and RDW as those of FIG. 1, yet the size distribution in FIG. 4 is abnormal, e.g., it is skewed to the left.

FIG. 5 is an abnormal RBC size distribution curve with the same MCV and RDW as those of FIG. 1, yet the size distribution in FIG. 5 is skewed to the right.

DETAILED DESCRIPTION OF THE INVENTION

The present invention provides a method for the determination of a novel hematological parameter useful in an improved particle analysis instrument. This method can identify abnormal particle populations in a sample of particles that normally display very consistent distributions.

This invention provides a method for analyzing an abnormal particle population in an experimental sample containing such particles. More specifically, the method provides a novel analysis of blood cells based upon the Gaussian distribution of one or more cell properties. These properties can include hemoglobin concentration, cell size, or other property with a Gaussian distribution. Even more specifically, this method allows the assessment of a distribution according to a property or characteristic of particles in an unknown or aberrant sample, by comparison to that property or characteristic of a normal population of the same type of particle. The method is based upon the characteristic of certain particle populations to distribute about a mean based on size or volume. This invention provides an indication of how the population is distributed or skewed about the mean. More specifically, the invention allows the differences in distribution to be analyzed for purposes of differentiating abnormal blood samples from normal blood samples. This analysis facilitates the evaluation of a disease state or treatment effect.

The method of this invention works particularly well on particle (e.g., cell) populations characterized by having a consistent property measurement distribution in the normal population. Preferably, the method of this invention is useful in the analysis of hematological cells, especially red blood cell populations. This characteristic of consistent distribution is found in the population of normal red blood cells.

For purposes of clarity, this invention is discussed with reference to red cell populations. However, it should be understood by one of skill in the art that the methods described herein can be applied to other types of particles, including other types of biological cells, and other types of hematology analysis instruments. For example, for other cell populations, the method can successfully differentiate normal populations from abnormal populations, depending upon the magnitude of the variation within the normal population. The greater the variation, the more difficult it will be to establish a particle property distribution index constant, described below, and allow identification of deviation from that norm. In one embodiment, the method can perform valuable analysis on samples that have a single population to analyze, e.g., RBC, certain populations of white blood cells, individual red blood cell hemoglobin content, and others.

Figure 1:
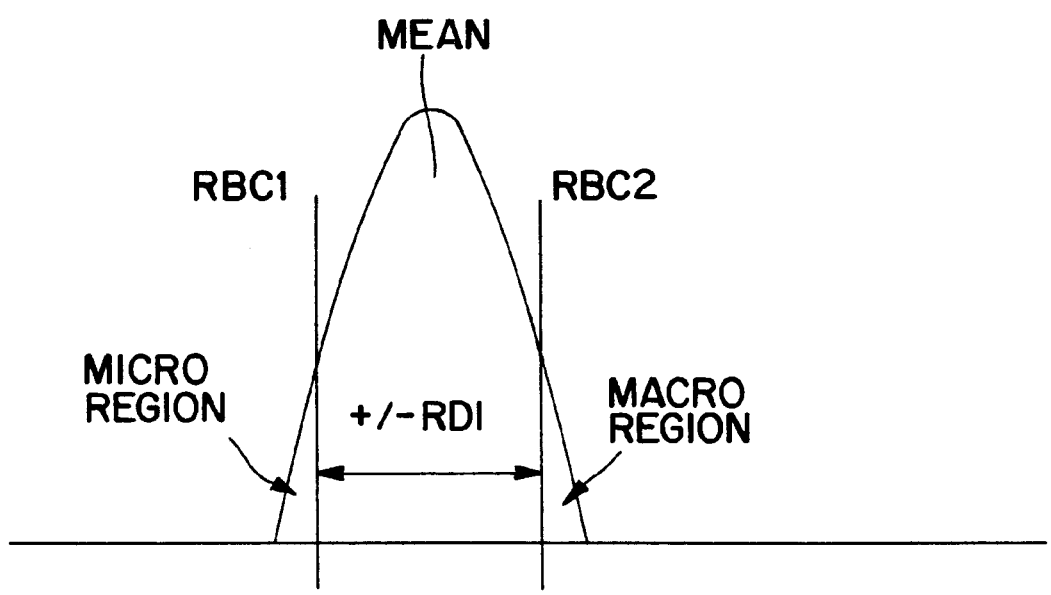
FIG. 1 is a "normal" RBC Gaussian size distribution curve generated by a conventional hematology analyzer. The region at beginning of distribution is described as the "Micro" region and the region at the end of the distribution is called the "Macro" region.
Figure 2:
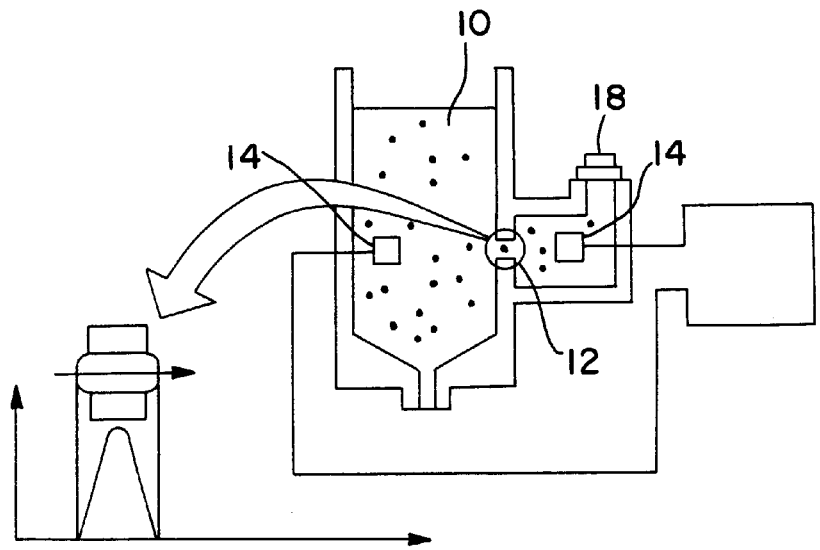
FIG. 2 is a graphical depiction of the operating principle (Coulter Principle) of a hematology analyzer. Indicated are the particle-containing solution to be analyzed 10, the aperture 12, the electrodes 14, the constant current 16, and the vacuum constant 18. The graph at the lower lefthand portion of the figure illustrates a pulse defined by the relationship between increased voltage and time as the particle flows through the aperture located between the electrodes.
Figure 3:
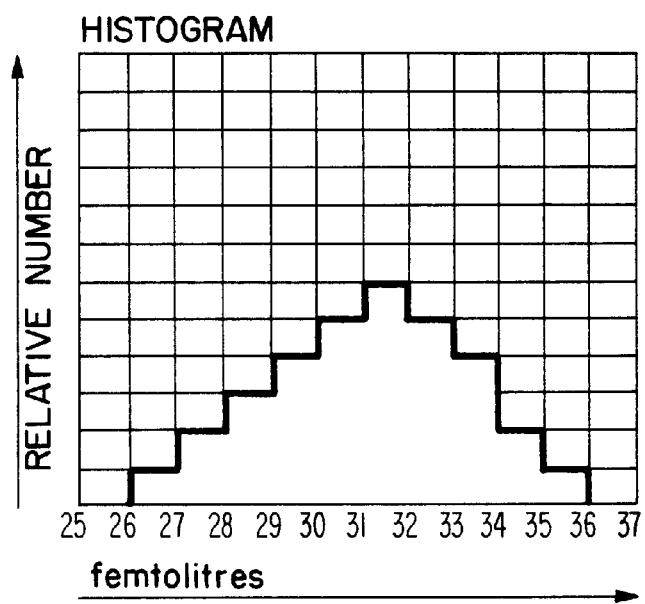
FIG. 3 is a diagram of a histogram illustrating frequency (relative number of pulses) of the y axis plotted against cell volume (size of pulses) on the x axis.

The preferred method employs a particle size analysis instrument. For purposes of clarity, this invention is discussed primarily with reference to a hematology analyzer as the preferred instrument for identifying the size distribution via a histogram of the red cell particles. Preferably such an instrument measures the size and frequency of electrical impedance pulses produced when each particle in a conductive diluent passes through a constant current. Among such instruments are a variety of conventional hematology instruments. See, for example, an instrument based on the Coulter principle as depicted in FIG. 2. The instrument provides pulse size data, which is recorded as a range of "channel" volume numbers based on the size of the pulses. As one example, in a Beckman Coulter Inc. hematology instrument called the $A^C.T$™ 5 diff instrument, RBC pulses are sorted into 128 channels (actually labeled 0 to 127) covering the size range of 30 to 300 femtoliters. These ranges are selected as appropriate values for both the population being measured (RBC) and the resolution required. The number of channels and the range of volume covered defines the volume per channel, i.e., resolution. As the number of channels increases for the same size range, the volume per channel decreases and the resolution increases. If the range covered by the 128 channels was doubled, the size of particles that could be analyzed would be larger. However, the resolution would be decreased because the volume per channel would be increased. To maintain the same resolution, the number of channels would be doubled to 256. With a decrease in channel numbers, however, the relative number of pulses in each channel increases as the same number of pulses is distributed over fewer channels. Selection of size range and channel numbers used in such an instrument is important. A size range that is too narrow can exclude some of the population, and too large a size range can cause loss of resolution if the number of channels is too low. Moreover, too many channels can result in too much resolution and insufficient data per channel to use effectively. Pulse frequency data is also collected by such an instrument. A plot of pulse frequency vs. channel number produces a particle size distribution curve. Such a plot can be linear or logarithmic. One such histogram is depicted in FIG. 3 and a resulting size distribution curve is depicted in FIG. 1.

Still other types of property (e.g., size) measurement and analysis instruments can be used to accumulate the information necessary to perform the method of this invention. For example, other particle size analysis instruments that employ one or more measurement parameters of light scatter, fluorescence, volume measured by D.C. (Coulter) volume, high frequency (radio frequency) and size can also be employed in the methods of this invention. Such instruments and apparatus of which many types are commercially available, can be employed as the instrument in this method. It should be understood that one of skill in the art can readily select the appropriate instrument, channel number and size range for any given sample containing particles without undue experimentation. Such selection is well within the ability of one of skill in the art, given the information provided herein.

According to the present method, a particle property measurement distribution index is employed to analyze the selected property of the experimental "or test" sample. This index is based on an average particle property (e.g., size) measurement distribution curve for multiple samples producing "normal" red blood cell histograms. More specifically, according to the preferred embodiment, a particle property distribution index is employed to analyze the experimental "or test" sample. This index is based on an average particle property distribution curve for multiple samples producing "normal" red blood cell histograms. For example, at least two normal samples are conventionally analyzed in a hematology analyzer to generate the histogram and distribution curve based on the property of size. Preferably, a statistically significant number of samples are used to develop the index. In a preferred embodiment, at least 50 samples are used. Due to the differences in instrument design, volume ranges within the instrument and number of channels used, the particle property distribution index is preferably determined from samples tested in the same type of instrument. More preferably, the particle property distribution index is determined in the same type instrument in which the experimental sample is evaluated. The particle property distribution index is double the average standard deviation for at least two normal particle property distributions recorded by the instrument. The following description of the determination of the index refers, for simplicity, to the property of particle size for a red blood cell population as analyzed in a hematology instrument.

Generally, a measure of the distribution about the mean is determined by calculating the standard deviation (SD) of the distribution from the data (e.g., histogram data) collected from the analysis of the experimental sample. The equation below is employed in such analysis:

$$SD = \text{the square root of } [\{C-(A \times D \times D)\}/(A-1)],$$

wherein A represents the sum of all pulses measured in the RBC histogram for every normal sample; B is the sum of the number of pulses multiplied by the channel number for every normal sample; and C is the sum of the number of pulses multiplied by the channel number squared for every normal sample. D represents the mean channel number, which is calculated as B/A-1. The resulting SD value is measured in channels.

Using the above formula, the average standard deviation (ASD) for a series of normal red blood cell size distributions is determined. This value is used to determine the particle property (e.g., size) distribution index, e.g., a Red Cell Distribution Index (RDI). The RDI represents the typical width (in channels) of a normal red cell histogram. The RDI is calculated by doubling the ASD.

Once an appropriate particle property distribution index (e.g., an RDI) has been evaluated for a particular analysis instrument and a particle sample type, an experimental particle property (e.g., size) distribution curve is analyzed from an experimental sample, e.g., an unknown sample of RBC from a patient under evaluation. As stated above, this curve can be generated from the pulse number and frequency data collected in a conventional hematology analysis instrument, according to the instructions of the instrument manufacturer and using conventional formats.

According to the method of this invention, the distribution curve of this experimental sample is analyzed to identify particle populations at the Micro (lower or left side) or Macro (upper or right side) regions of the curve that differ from particle populations in the same regions of an average RBC size distribution curve. This analysis involves identifying a lower threshold position (RBC1) of the experimental sample distribution curve and identifying a critical parameter for analysis of the experimental curve. The lower threshold position is identified as a channel number that is the difference between the mean channel of the experimental curve (D) (i.e., D=(B/A−1), where A represents the sum of all pulses measured in the RBC histogram for the experimental sample; and B is the number of pulses multiplied by the channel number for the experimental sample) and the RDI. The following equation describes this determination:

$$RBC1 = \text{Mean channel of experimental curve} - RDI$$

Thus, the first critical parameter, referred to herein as the "Micro Region" population, is formed by the particles in the region spanning the beginning of the experimental sample distribution curve, i.e., the "data beginning channel" to the lower threshold position (RBC1).

Further, according to this method, the analysis involves identifying an upper threshold position (RBC2) of the experimental sample distribution curve and identifying a second critical parameter for analysis of the experimental curve. The upper threshold position is identified as a channel number that is the sum of the RDI and the mean channel number of the experimental sample, as defined above. The following equation describes this determination:

$$RBC2 = \text{Mean channel of experimental curve} + RDI$$

Thus, the second critical parameter, referred to herein as the "Macro Region" population, is formed by the particles in the region spanning the upper threshold position to the end of the distribution curve. The end of the distribution curve is measured as the data end channel.

The analysis of the Micro and Macro regions of the distribution curve of the experimental sample provides novel RBC parameters, which is the number or percentage of total RBC in the Micro or Macro region. According to the present method, these numbers are determined for one or both regions for both the experimental sample and for the average distribution curve that produced the RDI.

This analysis can be performed for the Micro Region of the experimental sample by using the equation below.

% Particles in Micro region=[(sum of particles from beginning of the experimental sample distribution curve to the lower threshold position)/(sum of all pulses)]×100.

The number or percentage of RBC particles within the Micro Region of the experimental distribution curve permits the identification of a characteristic of the sample in comparison to the normal values. An increase or decrease in the % particles of the Micro Region of the experimental sample in relation to the normal samples provides an indication of an abnormal particle population in the region.

This analysis can be performed for the Macro Region of the experimental sample by using the following equation.

% Particles in Macro region=[(sum of particles from the upper threshold position to the end of the experimental sample distribution curve)/(sum of all cells)]×100.

The number or percentage of RBC particles within the Macro Region of the experimental distribution curve permits the identification of a characteristic of the sample in comparison to the normal values. An increase or decrease in the % particles of the Macro Region of the experimental sample in relation to the average or standard samples provides an indication of an abnormal particle population in the region.

The values obtained for the % Micro and % Macro are then used to assess the distribution or skew of the histogram about the mean. A sample with a normal red cell distribution results in the calculation of % Micro and % Macro that are similar to those determined of a normal distribution. As the % Micro and % Macro values increase or decrease relative to the average values for those regions, these aberrant values provide an indication of increasing divergence from a normal distribution. Additionally, the increase or decrease in the % Micro and % Macro values is significant where the change from normal occurs on both sides of the population or only on one side.

For example, FIGS. 4 and 5 are histograms of two RBC experimental populations. By applying the method of this invention, one can analyze the % cells in the Micro Region and the % cells in the Macro Region of the experimental cell populations. Using this method, differences from the normal range are clearly identified. In FIG. 4, the % Micro is within normal ranges and the % Macro is increased relative to a normal Gaussian curve of FIG. 1. In FIG. 5, the % Micro is increased and the % Macro is within normal ranges relative to FIG. 1. This additional information about the skew of the histograms is not apparent from the MCV and RDW values conventionally obtained by the prior art hematological analysis. This additional information thus enables a further differentiation of abnormal blood samples from normal blood samples which can facilitate diagnosis of a disease state or treatment effect.

As another aspect of this invention, a computer program is provided that performs the analysis and calculations described above. This program generates and evaluates the Micro and Macro regions of the particle populations. More specifically, the computer program is designed to record, sort and calculate the parameters of the equations provided above, e.g., the SD, the mean channel value, the lower and upper thresholds, the RDI, and to obtain the necessary analytical results. In a preferred embodiment, this computer program is integrated into the particle analysis instrument, particularly a hematology instrument. In still other embodiments, the program is on a separate computer, which is a "plug-in" device for attachment to the analysis instrument. Still another embodiment of this invention is a computer program that is present on a standalone computer, into which data from the instrument is fed. Alternatively, the method of this invention can be generated by use of conventional spreadsheet programs on standalone personal computers.

This computer program comprises means for translating electrical pulse data (e.g., size data) recorded as a range of channel volume numbers and pulse frequency data into a plot of pulse frequency vs. channel number. A particle property (e.g., size) distribution curve is produced by use of this data. This program also comprises a means for analyzing the particle property distribution curve of the experimental sample in a particle analysis instrument. The program also comprises in one embodiment means for identifying particle populations at the lower or upper region of the distribution curve that differ from particle populations in the same regions of an average particle property distribution curve based on multiple normal samples containing the particles. The program further contains means for determining the number or percentage of particles within the lower Micro or upper Macro region of the experimental distribution curve to identify a characteristic of the sample. In yet a further embodiment, the computer program contains means for determining a particle property (e.g., size) distribution index based on an average particle property distribution curve for multiple normal samples containing particles in the particle analysis instrument. The program preferably also contains means for comparing the average particle property distribution curve and the experimental particle property distribution curve by analyzing curve data using the index. Thus, the program preferably performs all of the calculations necessary to perform the method of this invention by analyzing the data on the test or experimental samples of particles. In still another embodiment of this program, it can provide an electrical signal or warning when an aberrant Micro region or Macro region parameter is identified.

Thus, as another aspect of this invention, a novel particle analysis instrument is provided which measures a particular characteristic or property of a particle on the basis of light scatter, fluorescence, volume measured by D.C. (Coulter) volume, high frequency (radio frequency), size, fluorescence, and combinations thereof This instrument produces pulse data of a property of the particle recorded as a range of channel numbers and pulse frequency data. The instrument can generate a linear or logarithmic plot of pulse frequency vs. channel number to produce a particle characteristic or property distribution curve. For example, the particular characteristic or property of a particle can include its size, granularity, and internal composition. In the case of a red blood cell, this property can include its hemoglobin content. Preferably, the instrument is a hematology instrument that measures the size and frequency of electrical impedance pulses produced when each particle in a conductive diluent passes through a current. The particle analysis instrument of this invention also has incorporated therein a computer chip containing an integrated computer program or a computer containing the computer program, as described above. Alternatively, the particle analysis instrument is designed to receive a plug-in computer containing the above-described program. Thus, the instrument itself not only provides the analytical information necessary to perform the method of this invention, but does all the necessary calculations and provides a signal or warning of an aberrant Micro region or Macro region parameter.

The computer program, alone or integrated into a particle analysis instrument, provides these newly identified parameters of the % or number of cells in the Micro Region and the % or number of cells in the Macro Region, to the user in many ways. As one embodiment, these values are indicated as a computer or instrument-generated highlighted warning, in circumstances in which the % or number of cells in the Micro Region and/or the % or number of cells in the Macro Region values exceed predetermined limits. As one example, such a highlighted "flag" would appear if the % cells in the Micro or Macro Region is greater than 5% above the value for that region in an average sample.

In another embodiment, the program can generate a series of highlighted warnings or flags along a scale of severity of standard values preestablished for the Macro and Micro Regions. For example, if the % cells in the Micro or Macro Regions was greater than 5% that of the standard, the result is identified by one highlighted warning. If the value for that region was between 5% and 10% greater than the standard, a different highlighted warning could appear. Further if the deviation of the value for either region exceeded 10% of the standard, a different flag would be generated by the program. The boundaries of the severity warning flags can be adjusted depending upon the severity of the conditions associated with such aberrant cell populations in those regions.

An increase or decrease in the percentage or number in one or both novel Micro and Macro parameters in relation to the standard values for the average particle distribution curve indicates an abnormal particle population. Such an abnormal population of particles is a characteristic of the experimental sample. This characteristic can be used to differentiate abnormal blood cell populations from normal blood cell populations to facilitate diagnosis of disease in which an aberrant RBC population in one or both regions is a symptom. Typically, such diseases would include the various types of anemia.

The following examples illustrate embodiments of the method of this invention. These examples are illustrative only, and do not limit the scope of the present invention.

EXAMPLE 1

Application of the Method to a "Normal" Histogram

Figure 6:
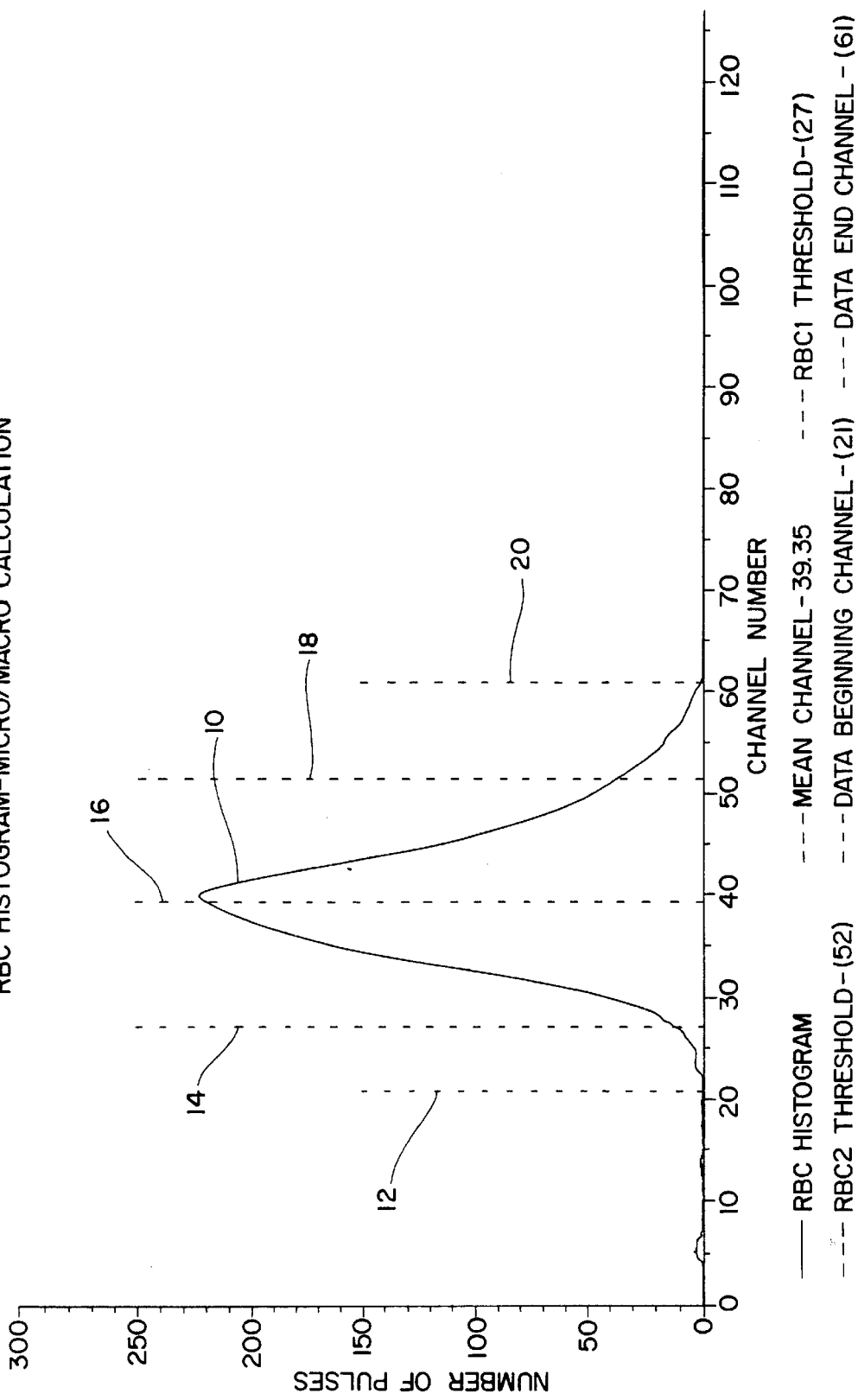
FIG. 6 is an RBC histogram 10 (size distribution curve) analyzed by the method of this invention. The parameters useful in the method are identified, e.g., the channel at which data collection begins 12, the lower threshold position 14, the mean channel 16, the upper threshold 18, and the channel at which data collection ended 20. The use of these parameters in the method of the invention is illustrated in Example 1.

This example demonstrates the method of the present invention applied to a "normal" red blood cell sample analyzed on a hematology analyzer ($A^C.T$™ 5 diff, Beckman Coulter Inc.). The channel number used in the analyzer was 128 (channels 0–127) over a volume range of 30 to 300 femtoliters. The histogram generated by the instrument for this sample is FIG. 6, and the parameters used in the method are indicated on the figure. For purposes of this example, the hematology analyzer data was sorted on an Excel® spreadsheet (Microsoft Corporation), and reported in Table I below. In the spreadsheet (Table 1), Column 1 is the channel number (0–127) and Column 2 is the number of pulses in each of these channels, i.e., the number of cells in the sample having the volume represented by that channel. The histogram of FIG. 6 is generated by plotting the Channel number (X-axis) against the number of pulses in the channel (Y-axis).

TABLE I

| Channel # | # Pulses | # Pulses x Channel # | # Pulses x (Channel #)² |
|---|---|---|---|
| 0 | 0 | 0 | 0 |
| 1 | 0 | 0 | 0 |
| 2 | 0 | 0 | 0 |
| 3 | 0 | 0 | 0 |
| 4 | 3 | 12 | 48 |
| 5 | 3 | 15 | 75 |
| 6 | 1 | 6 | 36 |
| 7 | 0 | 0 | 0 |
| 8 | 0 | 0 | 0 |
| 9 | 0 | 0 | 0 |
| 10 | 0 | 0 | 0 |
| 11 | 0 | 0 | 0 |
| 12 | 1 | 12 | 144 |
| 13 | 2 | 26 | 338 |
| 14 | 1 | 14 | 196 |
| 15 | 1 | 15 | 225 |

TABLE I-continued

| Channel # | # Pulses | # Pulses x Channel # | # Pulses x (Channel #)$^2$ |
|---|---|---|---|
| 16 | 0 | 0 | 0 |
| 17 | 0 | 0 | 0 |
| 18 | 0 | 0 | 0 |
| 19 | 0 | 0 | 0 |
| 20 | 0 | 0 | 0 |
| 21 Begin | 0 | 0 | 0 |
| 22 | 2 | 44 | 968 |
| 23 | 3 | 69 | 1587 |
| 24 | 3 | 72 | 1728 |
| 25 | 6 | 150 | 3750 |
| 26 | 9 | 234 | 6084 |
| 27 RBC1 | 16 | 432 | 11664 |
| 28 | 23 | 644 | 18032 |
| 29 | 38 | 1102 | 31958 |
| 30 | 55 | 1650 | 49500 |
| 31 | 75 | 2325 | 72075 |
| 32 | 102 | 3264 | 104448 |
| 33 | 131 | 4323 | 142659 |
| 34 | 160 | 5440 | 184960 |
| 35 | 177 | 6195 | 216825 |
| 36 | 194 | 6984 | 251424 |
| 37 | 207 | 7659 | 283383 |
| 38 | 216 | 8208 | 311904 |
| 39 | 223 | 8697 | 339183 |
| 40 | 210 | 8400 | 336000 |
| 41 | 188 | 7708 | 31628 |
| 42 | 166 | 6972 | 292824 |
| 43 | 146 | 6278 | 269954 |
| 44 | 124 | 5456 | 240064 |
| 45 | 103 | 4635 | 208575 |
| 46 | 87 | 4002 | 184092 |
| 47 | 74 | 3478 | 163446 |
| 48 | 61 | 2928 | 140544 |
| 49 | 49 | 2401 | 117649 |
| 50 | 42 | 2100 | 105000 |
| 51 | 35 | 1785 | 91035 |
| 52 RBC2 | 27 | 1404 | 73008 |
| 53 | 20 | 1060 | 56180 |
| 54 | 15 | 810 | 43740 |
| 55 | 13 | 715 | 39325 |
| 56 | 8 | 448 | 25088 |
| 57 | 6 | 342 | 19494 |
| 58 | 4 | 232 | 13456 |
| 59 | 3 | 177 | 10443 |
| 60 | 1 | 60 | 3600 |
| 61 END | 0 | 0 | 0 |
| 62 | 0 | 0 | 0 |
| 63 | 0 | 0 | 0 |
| 64 | 0 | 0 | 0 |
| 65 | 0 | 0 | 0 |
| 66 | 0 | 0 | 0 |
| 67 | 0 | 0 | 0 |
| 68 | 0 | 0 | 0 |
| 69 | 0 | 0 | 0 |
| 70 | 0 | 0 | 0 |
| 71 | 0 | 0 | 0 |
| 72 | 0 | 0 | 0 |
| 74 | 0 | 0 | 0 |
| 75 | 0 | 0 | 0 |
| 76 | 0 | 0 | 0 |
| 77 | 0 | 0 | 0 |
| 78 | 0 | 0 | 0 |
| 79 | 0 | 0 | 0 |
| 80 | 0 | 0 | 0 |
| 90 | 0 | 0 | 0 |
| 91 | 0 | 0 | 0 |
| 92 | 0 | 0 | 0 |
| 93 | 0 | 0 | 0 |
| 94 | 0 | 0 | 0 |
| 95 | 0 | 0 | 0 |
| 96 | 0 | 0 | 0 |
| 97 | 0 | 0 | 0 |
| 98 | 0 | 0 | 0 |
| 99 | 0 | 0 | 0 |
| 100 | 0 | 0 | 0 |
| 101 | 0 | 0 | 0 |
| 102 | 0 | 0 | 0 |
| 103 | 0 | 0 | 0 |
| 104 | 0 | 0 | 0 |
| 105–127 | 0 | 0 | 0 |

According to the method of this invention, the channels that encompass the major population are then determined by locating the channel number that contains the most pulses. The first channel to the left of the main peak that has 0 (zero) pulses is identified as the "Beginning" channel number (#), i.e., Channel 21. The first channel to the right of the main peak that has 0 (zero) pulses is identified as the "End" channel number (#), i.e., Channel 61. The instrument and the computer program contained thereof then calculate from the data in Table I:

Parameter A: the sum of all pulses in channels from "Beginning" channel to "End" Channel=3022.

Parameter B: the product of (Channel number×number of pulses) from "Beginning" channel to "End" Channel is=118883

Parameter C: the product of (number of pulses×(Channel number )$^2$) from "Beginning" channel to "End" Channel=4781697

Parameter D: the Histogram Mean Channel, calculated as [B/(A−1)], which is 39.35.

Parameter E: the Histogram Standard Deviation, calculated as the square root $$[\{C-(A\times(D^2)\}/(A-1)],$$

which is 5.81.

An average value for the standard deviation (in channel numbers) is established by analysis of at least two, and preferably at least 30, and most preferably at least 50, normal Red Cell distributions according to this method. This value is doubled for use as the Red cell Distribution Index (RDI), i.e., the particle size distribution index. From data collected, the number of channels defined from the normal population is Parameter F=12.2 channels.

Using the histogram of FIG. 6 and the data of Table I, the position of the Lower Threshold RBC1 is determined by the difference between the Histogram Mean Channel and the RDI, or D−F=39.35−12.2=27.

The position of the Upper Threshold RBC2 is determined by the sum of the Histogram Mean Channel and the RDI, or (D+F)=39.35+12.2=52. The channel number is rounded to a whole channel number.

The area of the histogram contained between RBC1 (channel 27) and "Beginning" (channel 21) represents the Micro region. The number of cells in this region is determined by summing the number of pulses in channels 21 through 27, which is 23.

The area of the histogram contained between RBC2 (channel 52) and "End" (channel 61) represents the Macro region. The number of cells in this region is determined by summing the number of pulses in channels 52 through 61, which is 70.

The percentage of cells in the Micro region is determined as the product of the number of cells in the Micro region over the sum of all pulses in the Micro region, which product is multiplied by 100, e.g., (23/3022)×100 or 0.76%.

The percentage of cells in the Macro region is determined as the product of the number of cells in the Macro region over the sum of all pulses in the Macro region, which product is multiplied by 100, e.g., (70/3022)×100 or 2.32%.

The % Micro and % Macro are compared with values established for an average normal RBC histogram to determine if the percentage of cells in the Micro or Macro region of the sample is increased or decreased significantly relative to the normal value.

EXAMPLE 2

Application of the Method to an Abnormal Histogram

Figure 7:
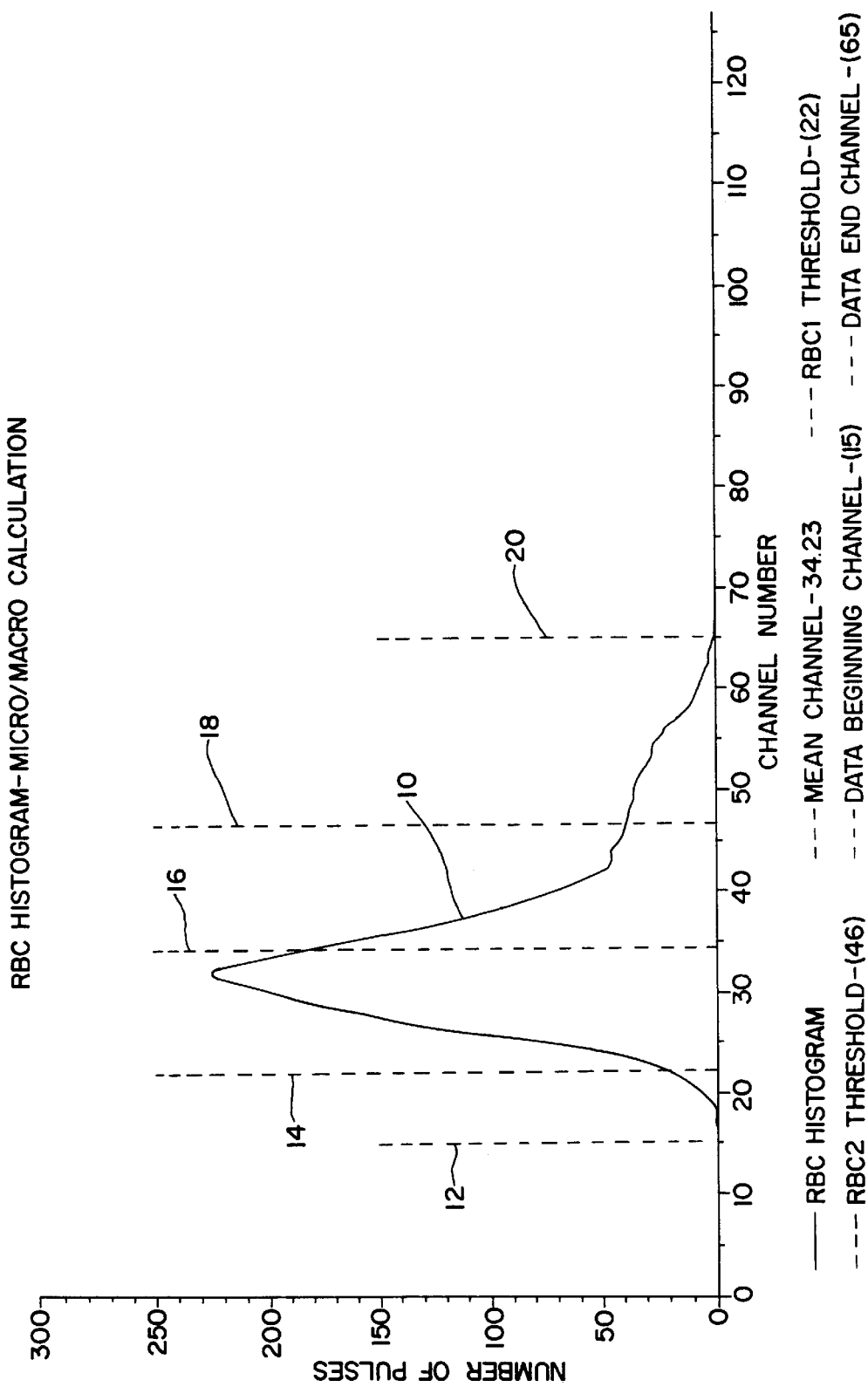
FIG. 7 is an abnormal RBC histogram 10 (size distribution curve) analyzed according to the method of this invention. The parameters useful in the method are identified, e.g., the channel at which data collection begins 12, the lower threshold position 14, the mean channel 16, the upper threshold 18, and the channel at which data collection ended 20. The use of these parameters in the method of the invention is illustrated in Example 2.

This example demonstrates the method of the present invention applied to an "abnormal" red blood cell sample having an increased number of cells in the Macro region on a hematology analyzer ($A^C.T^{TM}$ 5 diff, Beckman Coulter Inc.). The channel number used in the analyzer was 128 (channels 0–127) over a volume range of 30 to 300 femtoliters. For purposes of this example, the hematology analyzer data was sorted on an Excel® spreadsheet and reported in Table II below. In the spreadsheet (Table II), Column 1 is the channel number (0–127) and Column 2 is the number of pulses in each of these channels, i.e., the number of cells in the sample having the volume represented by that channel. The histogram of FIG. 7 is generated by plotting the Channel number (X-axis) against the number of pulses in the channel (Y-axis).

TABLE II

| Channel # | # Pulses | # Pulses x Channel # | # Pulses x (Channel #)$^2$ |
| --- | --- | --- | --- |
| 0 | 0 | 0 | 0 |
| 1 | 0 | 0 | 0 |
| 2 | 0 | 0 | 0 |
| 3 | 0 | 0 | 0 |
| 4 | 1 | 4 | 16 |
| 5 | 0 | 0 | 0 |
| 6 | 0 | 0 | 0 |
| 7 | 0 | 0 | 0 |
| 8 | 0 | 0 | 0 |
| 9 | 0 | 0 | 0 |
| 10 | 0 | 0 | 0 |
| 11 | 0 | 0 | 0 |
| 12 | 0 | 0 | 0 |
| 13 | 0 | 0 | 0 |
| 14 | 0 | 0 | 0 |
| 15 | 0 | 0 | 0 |
| Begin | | | |
| 16 | 1 | 16 | 256 |
| 17 | 1 | 17 | 289 |
| 18 | 3 | 54 | 972 |
| 19 | 7 | 133 | 2527 |
| 20 | 14 | 280 | 5600 |
| 21 | 20 | 420 | 8820 |
| 22 | 30 | 660 | 14520 |
| RBC1 | | | |
| 23 | 48 | 1104 | 25392 |
| 24 | 68 | 1632 | 64375 |
| 25 | 103 | 2575 | 64375 |
| 26 | 136 | 3536 | 91936 |
| 27 | 155 | 4185 | 223995 |
| 28 | 181 | 5068 | 141904 |
| 29 | 197 | 5713 | 165677 |
| 30 | 216 | 6480 | 194400 |
| 31 | 223 | 6913 | 214303 |
| 32 | 209 | 6688 | 214016 |
| 33 | 188 | 6204 | 204732 |
| 34 | 169 | 5746 | 195364 |
| 35 | 143 | 5005 | 175175 |
| 36 | 119 | 4284 | 154224 |
| 37 | 101 | 3737 | 138269 |
| 38 | 83 | 3154 | 119852 |
| 39 | 71 | 2769 | 107991 |
| 40 | 60 | 2400 | 96000 |
| 41 | 48 | 1968 | 80688 |
| 42 | 45 | 1890 | 79380 |
| 43 | 45 | 1935 | 83205 |
| 44 | 41 | 1804 | 79376 |
| 45 | 39 | 1755 | 78975 |
| 46 | 38 | 1748 | 80408 |
| RBC2 | | | |
| 47 | 37 | 1739 | 81733 |
| 48 | 35 | 1680 | 80640 |
| 49 | 35 | 1715 | 84035 |
| 50 | 33 | 1650 | 82500 |
| 51 | 30 | 1530 | 78030 |
| 52 | 27 | 1404 | 73008 |
| 53 | 27 | 1431 | 75843 |
| 54 | 23 | 1242 | 67068 |
| 55 | 20 | 1100 | 60500 |
| 56 | 14 | 784 | 43904 |
| 57 | 10 | 570 | 32490 |
| 58 | 8 | 464 | 26912 |
| 59 | 6 | 354 | 20886 |
| 60 | 5 | 300 | 18000 |
| 61 | 3 | 183 | 11163 |
| 62 | 3 | 186 | 11532 |
| 63 | 2 | 126 | 7938 |
| 64 | 1 | 64 | 4096 |
| 65 | 0 | 0 | 0 |
| END | | | |
| 66 | 0 | 0 | 0 |
| 67 | 0 | 0 | 0 |
| 68 | 0 | 0 | 0 |
| 69 | 0 | 0 | 0 |
| 70 | 0 | 0 | |
| 71 | 0 | 0 | 0 |
| 72 | 0 | 0 | 0 |
| 74 | 0 | 0 | 0 |
| 75 | 0 | 0 | 0 |
| 76 | 0 | 0 | 0 |
| 77 | 0 | 0 | 0 |
| 78 | 0 | 0 | 0 |
| 79 | 0 | 0 | 0 |
| 80 | 0 | 0 | 0 |
| 90 | 0 | 0 | 0 |
| 91 | 0 | 0 | 0 |
| 92 | 0 | 0 | 0 |
| 93 | 0 | 0 | 0 |
| 94 | 0 | 0 | 0 |
| 95 | 0 | 0 | 0 |
| 96 | 0 | 0 | 0 |
| 97 | 0 | 0 | 0 |
| 98 | 0 | 0 | 0 |
| 99 | 0 | 0 | 0 |
| 100 | 0 | 0 | 0 |
| 101 | 0 | 0 | 0 |
| 102 | 0 | 0 | 0 |
| 103 | 0 | 0 | 0 |
| 104 | 0 | 0 | 0 |
| 105–127 | 0 | 0 | 0 |

According to the method of this invention, the channels that encompass the major population are determined by locating the channel number that contains the most pulses. The first channel to the left of the main peak that has 0 (zero) pulses is identified as the "Beginning" channel number (#), i.e., Channel 15. The first channel to the right of the main peak that has 0 (zero) pulses is identified as the "End" channel number (#), i.e., Channel 65. The instrument and the computer program contained thereof then calculate:

Parameter A: the sum of all pulses in channels from "Beginning" to "End", which is 3066.

Parameter B: the product of the number of pulses×the channel number in channels from "Beginning" to "End," which is 104916.

Parameter C: the product of the number of pulses×the channel number squared in channels from "Beginning" to "End," which is 3777874.

Parameter D: the Histogram Mean Channel, calculated as [B/(A−1)], which is 34.23.

Parameter E: the Histogram Standard Deviation, calculated as the square root $$[\{C-(A\times D\times D)\}/(A-1)],$$

which is 7.78.

By analysis of a number of normal Red Cell distributions according to this method as described above, an average value for the standard deviation (in channel numbers) is established. This value is doubled for use as the Red cell Distribution Index (RDI), i.e., the particle size distribution index. From data collected, the RDI has been established for this system to be 12.2 channels.

Using the histogram of FIG. 7, the position of the Lower Threshold RBC1 is determined by the difference between the Histogram Mean Channel (calculated above) and the RDI. The position of the Upper Threshold RBC2 is determined by the sum of the Histogram Mean Channel and the RDI. The channel number is rounded to a whole channel number.

Channel number for RBC1=34.23−12.2=22

Channel number for RBC2=34.23+12.2=46

The area of the histogram contained between RBC1 (channel 22) and "Beginning" (channel 15) represents the Micro region. The number of cells in this region is determined by summing the number of pulses in channels 15 through 22, which is 46.

The area of the histogram contained between RBC2 (channel 46) and "End" (channel 65) represents the Macro region. The number of cells in this region is determined by summing the number of pulses in channels 46 through 55, which is 319.

The percentage of cells in the Micro region is determined as the number of cells in the Micro region over the sum of all pulses in the Micro region, which product is multiplied by 100, e.g., (46/3066)×100 or 1.50%.

The percentage of cells in the Macro region is determined as the number of cells in the Macro region over the sum of all pulses in the Macro region, which product is multiplied by 100, e.g., (319/3066)×100 or 10.40%.

The % Micro and % Macro are compared with values established for an average normal RBC histogram to determine if the percentage of cells in the Micro or Macro region of the sample is increased or decreased significantly relative to the normal value.

In this example, the RBC histogram of FIG. 7 is extended on the right side. This skew of the distribution has been detected by the calculation as an increase in the number of cells in the Macro region. Such a skewed Macro parameter can be an indication of disease.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for analyzing an abnormal particle population in an experimental sample containing said particles comprising the steps of:

generating a particle property distribution curve of said experimental sample in a particle analysis instrument, wherein said instrument provides electrical pulse data of a property of said particle recorded as a range of channel volume numbers and pulse frequency data; and wherein a plot of pulse frequency versus channel number produces said particle property distribution curve;

determining a number or percentage of particles in a micro region and/or a macro region of said particle property distribution curve, said micro region located between the beginning of the curve and a lower threshold position, said macro region located between an upper threshold position and the end of the curve; and comparing the number or percentage of particles in the micro region and/or the macro region of said curve from said experimental sample with the number or percentage of particles in the corresponding micro region and/or macro region of an average particle property distribution curve based on multiple normal samples containing normal particles.

2. The method for analyzing an abnormal particle population according to claim 1, wherein said upper threshold position is located on the curve at the point located at the mean minus the particle property distribution index; wherein said lower threshold position is located on the curve at the point located at the mean plus the particle property distribution index; and wherein the distribution index is based on an average particle size distribution curve for multiple normal samples containing normal particles in said particle analysis instrument.

3. The method according to claim 2, wherein said particle property distribution index is double the standard deviation of at least two normal particle property distributions recorded by said instrument.

4. The method according to claim 1, wherein said instrument measures a parameter of each particle selected from the group consisting of direct current, radio frequency current, light scatter, fluorescence, and combinations thereof.

5. The method according to claim 3, wherein said standard deviation is calculated according to the equation:

Standard Deviation=the square root of $[\{C-(A\times D\times D)\}/(A-1)],$ wherein A is the sum of all pulses; B is the sum of the number of pulses multiplied by the volume measured as a channel number; C is the sum of the number of pulses multiplied by the channel number squared, and D is the mean channel number.

6. The method according to claim 1, wherein said determining step further comprises calculating the percentage of particles present in the micro region by the formula:

% particles in region=[(sum of particles from beginning of the experimental sample distribution curve to said lower threshold position)/(sum of all pulses)]×100.

7. A method for identifying and analyzing an abnormal particle population in an experimental sample containing said particles comprising the steps of:

generating a particle size distribution curve of said experimental sample in a particle analysis instrument, wherein said instrument provides electrical pulse data of a property of said particle recorded as a range of channel volume numbers and pulse frequency data; and wherein a plot of pulse frequency versus channel number produces said particle size distribution curve;

determining a number or percentage of particles in a micro region and/or a macro region of said particle size distribution curve, said micro region located between the beginning of the curve and a lower threshold position, said macro region located between an upper threshold position and the end of the curve; and comparing the number or percentage of particles in the micro region and/or the macro region of said curve from said experimental sample with the number or percentage of particles in the corresponding micro region and/or macro region of an average particle size distribution curve based on multiple normal samples containing normal particles.

8. The method for identifying and analyzing an abnormal particle population according to claim 7, wherein said upper threshold position is located on the curve at the point located at the mean minus the particle size distribution index; wherein said lower threshold position is located on the curve at the point located at the mean plus the particle size distribution index; and wherein the distribution index is based on an average particle size distribution curve for multiple normal samples containing normal particles in said particle analysis instrument.

9. The method according to claim 8, wherein said particle size distribution index is double the standard deviation of at least two normal particle size distributions recorded by said instrument.

10. The method according to claim 7 wherein said plot is linear or logarithmic.

11. The method according to claim 7, wherein said instrument measures a parameter of each particle selected from the group consisting of direct current, radio frequency current, light scatter, and fluorescence and combinations thereof.

12. The method according to claim 9, wherein said standard deviation is calculated according to the equation:

Standard Deviation=the square root of $[\{C-(A \times D \times D)\}/(A-1)]$, wherein A is the sum of all pulses; B is the sum of the number of pulses multiplied by the volume measured as a channel number; C is the sum of the number of pulses multiplied by the channel number squared, and D is the mean channel number.

13. The method according to claim 7 wherein said determining step further comprises calculating the percentage of particles present in the micro region by the formula:

% particles in region=[(sum of particles from beginning of the experimental sample distribution curve to said lower threshold position)/(sum of all pulses)]×100.

14. The method according to claim 13, further comprising comparing said percentage of particles in the micro region with the same calculation for said average particle distribution curve, wherein an increase or decrease in said percentage of particles of said experimental sample in relation to said average indicates an abnormal particle population in said region.

15. The method according to claim 7, wherein said determining step further comprises calculating the percentage of particles present in the macro region by the formula:

% particles in region=[(sum of particles from the upper threshold position to the end of said experimental sample distribution curve)/(sum of all cells)]×100.

16. The method according to claim 15, further comprising comparing said % particles in the macro region at the end of said experimental sample distribution curve with the same calculation for said average particle distribution curve, wherein an increase or decrease in said % particles of said experimental sample in relation to said average provides an indication of an abnormal particle population in said region.

17. The method according to claim 1 wherein said steps are performed by a computer program.

18. The method according to claim 1 wherein said particles are cells.

19. The method according to claim 18, wherein said cells are red blood cells.

20. A computer program for identifying and analyzing an abnormal particle population in an experimental sample containing said particles comprising:

means for generating a particle property distribution curve of said experimental sample in a particle analysis instrument, wherein said instrument provides electrical pulse data of a property of said particle recorded as a range of channel volume numbers and pulse frequency data; and wherein a plot of pulse frequency versus channel number produces said particle property distribution curve;

means for determining a number or percentage of particles in a micro region and/or a macro region of said particle property distribution curve, said micro region located between the beginning of the curve and a lower threshold position, said macro region located between an upper threshold position and the end of the curve; and means for comparing the number or percentage of particles in the micro region and/or the macro region of said curve from said experimental sample with the number or percentage of particles in the corresponding micro region and/or macro region of an average particle property distribution curve based on multiple normal samples containing normal particles.

21. The computer program for identifying and analyzing an abnormal particle population according to claim 20, wherein said upper threshold position is located on the curve at the point located at the mean minus the particle property distribution index; wherein said lower threshold position is located on the curve at the point located at the mean plus the particle property distribution index; and wherein the distribution index is based on an average particle size distribution curve for multiple normal samples containing normal particles in said particle analysis instrument.

22. The program according to claim 21, further comprising:

means for determining a particle property distribution index based on an average particle property distribution curve for multiple normal samples containing said particles in said particle analysis instrument; and means for comparing the average particle property distribution curve and said experimental particle property distribution curve by analyzing curve data using said index.

23. The program according to claim 22, comprising means for identifying a deviation from said average normal samples in said lower or upper region by generating a signal.

24. A particle analysis instrument that comprises an integrated computer program of claim 20.

25. The instrument according to claim 24, further comprising means for providing electrical pulse size data recorded as a range of channel volume numbers and pulse frequency data, and wherein a plot of pulse frequency vs. channel number produces said particle property distribution curve.

26. The computer program according to claim 21, wherein said program comprises a parameter for analyzing conditions associated with aberrant red blood cell populations in a histogram, comprising the percentage of cells in the region of the histogram spanning the beginning of the experimental sample distribution curve to a threshold related to a particle size distribution index.

27. The computer program according to claim 26, wherein the parameter comprises a calculation from the formula:

$$\% RBC \text{ in region} = [(\text{sum of pulses from beginning of the experimental sample distribution curve to a lower threshold position})/(\text{sum of all pulses})] \times 100;$$

wherein said lower threshold position is the difference between said particle distribution index and the histogram mean channel number, and is calculated by the formula:

$$\{2 \times \text{square root of } [\{C-(A \times D \times D)\}/(A-1)]\} - D,$$

wherein A is the sum of all pulses in the histogram; B is the sum of the number of pulses×the channel number; C is the sum of the number of pulses×the channel number squared and D is the mean channel number.

28. The computer program according to claim 21, wherein said program comprises a parameter for analyzing conditions associated with aberrant red blood cell populations in a histogram, comprising the percentage of cells in the region of the histogram spanning a threshold related to a particle size distribution index and the end of the experimental sample distribution curve.

29. The computer program according to claim 21, comprising a calculation from the formula:

$$\% RBC \text{ in region} = [(\text{sum of pulses from an upper threshold positions to the end of the experimental sample distribution curve})/(\text{sum of all pulses})] \times 100;$$

wherein said upper threshold position is the sum of said particle distribution index and the histogram mean channel number, and is calculated by the formula:

$$\{2 \times \text{square root of } [\{C-(A \times D \times D)\}/(A-1)]\} + D,$$

wherein A is the sum of all pulses in the histogram; B is the sum of the number of pulses×the channel number; C is the sum of the number of pulses×the channel number squared, and D is the mean channel number.

* * * * *